United States Patent
Aftab et al.

US009795656B2

(10) Patent No.: US 9,795,656 B2
(45) Date of Patent: Oct. 24, 2017

(54) TREATMENT OF OCULAR DISEASES

(75) Inventors: Ahmed Aftab, Scottsdale, AZ (US);
Lucia Desser, Vienna (AT); Bernhard Lotz, Leonding (AT); Thomas Mohr, Guntramsdorf (AT)

(73) Assignee: MARLYN NUTRACEUTICALS INC, Phoenix, AZ (US)

( * ) Notice: Subject to any disclaimer, the term of this patent is extended or adjusted under 35 U.S.C. 154(b) by 1872 days.

(21) Appl. No.: 12/377,556

(22) PCT Filed: Aug. 16, 2007

(86) PCT No.: PCT/AT2007/000393
§ 371 (c)(1),
(2), (4) Date: Sep. 13, 2011

(87) PCT Pub. No.: WO2008/019417
PCT Pub. Date: Feb. 21, 2008

(65) Prior Publication Data
US 2011/0311509 A1 Dec. 22, 2011

(30) Foreign Application Priority Data
Aug. 16, 2006 (AT) ................. A 1376/2006

(51) Int. Cl.
*A61K 38/54* (2006.01)
*A61K 38/48* (2006.01)

(52) U.S. Cl.
CPC ........ *A61K 38/4873* (2013.01); *A61K 38/482* (2013.01); *A61K 38/4886* (2013.01)

(58) Field of Classification Search
CPC .............. A61K 38/482; A61K 38/4886; A61K 38/4873
See application file for complete search history.

(56) References Cited

U.S. PATENT DOCUMENTS

| 2003/0027998 A1 | 2/2003 | Holtzman et al. | |
| 2005/0008582 A1* | 1/2005 | Du-Thumm et al. | 424/48 |
| 2006/0083727 A1 | 4/2006 | Kajander et al. | |

FOREIGN PATENT DOCUMENTS

| JP | WO2006025276 | 3/2006 |
| WO | 98/58666 A1 | 12/1998 |
| WO | 02/076496 A1 | 10/2002 |
| WO | 02089833 | 11/2002 |
| WO | 2004113522 | 12/2004 |
| WO | 2005/100556 A2 | 10/2005 |
| WO | 2005110453 | 11/2005 |

OTHER PUBLICATIONS

Takano A. et al., Posterior Vitreous Detachment Induced by Nattokinase (Subtilisin NAT): A Novel Enzyme for Pharmacologic Vitreolysis, Investigative Ophthalmology & Visual Science, May 2006, vol. 47, No. 5, pp. 2075-2079.*
Prevent—the term defined by Merriam-Webster Online dictionary at the web: http://www.merriam-webster.com/dictionary/prevent; pp. 1-3; accessed on Jan. 8, 2013.*
V2: Keyt B.A. et al., The Carboxyl-terminal Domain (111-165) of Vascular Endothelial Growth Factor Is Critical for Its Mitogenic Potency, The Journal of Biological Chemistry, Mar. 29, 1996, vol. 271, No. 13, pp. 7788-7795.*
Stauder et al., Machine English translation of WO 1998/058666 A1, pertinent pp. 1-16 only.*
Yance D., A Novel Approach to Cancer Treatment: Botanicals that Inhibit Angiogenesis and/or Enhance Nonspecific Biological Immune Response, Mar. 3, 2005, pp. 1-42, published on the web at http://www.medicineabiomolecular.com.br/biblioteca/pdfs/Biomolecular/mb-0238.pdf.*
U2: Larsen H.R., Nattokinase-Interim survey, Virtual LAF Conference, Proceedings of 39th session, Mar. 10, 2005-Apr. 26, 2005, pp. 1-53; published on the web on Nov. 4, 2005 at- http://www.afibbers.org/conference/session39.pdf.*
Dzivite et al., "Regular Intake of Wobenzym May Prevent Late Complications in Diabetes Mellitus", Int. J. Immunotherapy, 17(2/3/4):143-148 (2001).
Bessatsu et al., Journal of Clinical and Experimental Medicine, Special Issue, New Developments in Angiogenic Studies, published by Ishiyaku Publ. Inc., pp. 90-96 (2002).
Grossman et al., "The Role of Nutrition in Treating Diseases of the Aging Eye: Senile Cataracts and Age-Related Macular Degeneration", New Ophthalmology, 22(4):421-428 (2005).
Notice of Reasons for Refusal for JP 2009-524045, dated Sep. 4, 2012.
Russian Office Action issued Feb. 24, 2012 in Russian Application No. 2009 109 358.
Mohr et al., "Plant proteolytic enzyme papain brogates angiogenic activation of human umbilical vein endothelial cells (HUVEC) in vitro", BMC Complementary & Alternative Medicine, 13 (231):1-9 (2013).
Bock et al., "Transport of proteolytic enzymes across Caco-2 cell monolayers", Pharm. Res., 15(9):1393-1400 (1998).
Office Action for Mexican Application No. MX/a/2009/001745 dated Aug. 18, 2014.

(Continued)

*Primary Examiner* — Satyendra K Singh
(74) *Attorney, Agent, or Firm* — Sughrue Mion, PLLC

(57) ABSTRACT

The present invention relates to the use of at least one protease for the manufacture of a medicament for the treatment and/or prevention of ocular diseases related to neoangiogenesis selected from the group consisting of age related macular degeneration (AMD), choroidal neovascularization, Hippel-Lindau Disease, iris neovascularization, ischemic proliferative retinopathy, neovascularization of the Cornea, and proliferative sickle cell retinopathy, wherein the at least one protease is selected from the group consisting of plant, non-mammalian animal and microbial proteases.

22 Claims, 4 Drawing Sheets

(56) References Cited

OTHER PUBLICATIONS

Starkow et al., "Papain Therapy of Eye Disease", Klinische Monatsblaetter Fuer Augenheilkunde, Ferdinand Enke Verlag, Stuttgart, 159(6):755-769 (1971), Abstract No. XP008089293.

* cited by examiner

TREATMENT OF OCULAR DISEASES

CROSS-REFERENCE TO RELATED APPLICATIONS

This is a 371 National Stage Entry of International Application No. PCT/AT2007/000393, filed Aug. 16, 2007, which claims priority of Austrian Patent Application No. A 1376/2006, filed Aug. 16, 2006, the contents of which are incorporated herein in their entirety

BACKGROUND OF THE INVENTION

The present invention relates to a medicament for the treatment of diseases related to neoangenesis.

Angiogenesis is defined as the formation of new blood vessels by outgrowth of endothelial cells from pre-existing vessels. During this process, endothelial cells degrade the underlying basement membrane, proliferate, migrate into neighboring tissue, and assemble into tubes. Finally, tube-to-tube connections are made and blood flow is established. The ability of mature tissues to adapt to changing demands requires both soluble factors like hypoxia inducible Factor (HIF) and Vascular endothelial factor (VEGF) and cell-cell as well as cell-matrix interactions.

VEGF was originally described as factor causing substantial vascular leakage and was named Vascular Permeability Factor (VPF). On account of its mitogenic effect in endothelial cells, the same protein was later renamed Vascular Endothelial Growth Factor (VEGF).

VEGF increases the permeability of the micro-vascular bed, thus promoting fluid and protein leakage from blood vessels. This results in the development of oedemas, wound fluid and seromas (e.g. after surgery), effusions (e.g. in chronic inflammatory diseases) and ascites (e.g. in cancer). VEGF is 10,000 times more potent than histamine in induction of vascular permeability.

Furthermore, VEGF is one of the most potent stimulators of endothelial cell proliferation. Finally, it stimulates the formation of capillaries from endothelial cells, thus promoting the cascade of events necessary for angiogenesis. Neoangiogenesis, the growth of new capillaries from pre-existing vessels in newly formed tissues or even deposits (like plaques etc.), contributes to the development and progression of a variety of pathological conditions. Under physiological conditions, angiogenesis is a tightly regulated process. In pathological conditions like cancer, rheumatoid arthritis, endometriosis, psoriasis or ocular neovascularisation this process is considerably enhanced and dysfunctional.

Growing evidence suggest that anti-angiogenic drugs will improve future therapies of diseases like cancer, rheumatoid arthritis, psoriasis and ocular neovascularisation and others. In vivo experiments demonstrated that hypoxia (e.g. in regions close to tumour necroses) is capable of inducing the expression of both VEGF and VEGF receptors (VEGFR-1) in different types of cells. Hypoxia causes the expression of Hypoxia-inducible factor-1 (HIF-1). Subsequently, HIF-1 complexes accumulate in the cell nucleus, bind to the HIF-1 binding site of the DNA, and initiate resp. upregulate transcription of VEGF-mRNA triggering an angiogenic switch that may cause adjacent blood vessels to sprout into the hypoxic tissue. Furthermore, VEGF expression can be induced/upregulated by various proinflammatory cytokines as it has been demonstrated in various models of chronic inflammation like psoriasis or rheumatoid arthritis.

VEGF can be removed from the circulation via the Alpha2-macroglobulin (a2M) pathway by protease-activated a2M. The a2M-protease complex is capable of binding VEGF in a vault at the surface. The resulting a2M-enzyme-VEGF complex is bound to the LRP receptor (low-density lipoprotein receptor-related protein receptor) expressed on the surface of cells like macrophages and endothelial cells, phagocytosed and destroyed. Oral Therapy with proteolytic Enzymes increases the number of activated a2M molecules thus elevating the cytokine/growth factor destroying capacity of the organisms (Desser L et al. Cancer Chemother Pharmacol Suppl (2001) 47:S10-515; Lauer D et al. Cancer Chemother Pharmacol Suppl (2001) 47:S4-S9).

Recently, several therapeutical approaches using VEGF receptor blockers or antibodies against VEGF have been proposed for the treatment of diseases involving increased angiogenesis, mainly cancer, but also for diseases involving angiogenesis in the eye such as macular degeneration.

Ocular neovascularisation or neoangiogenesis has been implicated as the most common cause of blindness and underlies the pathology of approximately 20 different eye diseases. E.g. in diabetes, new capillaries formed in the retina invade the vitreous humor, causing bleeding and blindness.

WO 2005/110453 relates to the use of human wild-type and mutein MT-SP1 proteases for cleaving VEGF and VEGF receptor. Such a cleaving leads to a reduction in angiogenesis and may thus be used to treat pathologies associated with angiogenesis.

JP 60112720 A relates to the use of papain and citric acid to treat diseases which are not associated with angiogenesis (e.g. glaucoma).

In the WO 2004/046199 the use of chondroitin sulfate to treat eye diseases is disclosed.

WO 2005/056784 relates to the use of nattokinase to treat diabetes.

In the SU 1342500 the use of papain to treat eye diseases like glaucoma is described.

U.S. Pat. No. 6,103,756 relates to a composition comprising antoxidant and flavonoids which may be used to treat eye disorders.

BRIEF SUMMARY OF THE INVENTION

1. Use of at least one protease for the manufacture of a medicament for the treatment and/or prevention of ocular diseases related to neoangiogenesis selected from the group consisting of age related macular degeneration (AMD), choroidal neovascularisation, Hippel-Lindau Disease, iris neovascularisation, ischemic proliferative retinopathy, neovascularisation of the Cornea, and proliferative sickle cell retinopathy, wherein the at least one protease is selected from the group consisting of plant, nonmammalian animal and microbial proteases.
2. Use set forth in item 1, characterized in that the at least one plant protease is selected from the group consisting of bromelain, papain, ficin and cucumisin.
3. Use set forth in item 1, characterized in that the microbial protease is selected from the group consisting of nattokinase, pronase, brinase, seaprose, serrapeptase and subtilisin.
4. Use set forth in item 1, characterized in that the nonmammalian animal protease is selected from the group consisting of reptilase, krill enzyme, batroxobin and lumbrokinase.
5. Use set forth in items 1 to 4, characterized in that the at least one plant, non-mammalian animal and/or microbial protease is included in the medicament in an amount from 10 to 90% w/w, preferably from 20 to 80% w/w, more preferably from 30 to 70% w/w.

6. Use set forth in any one of items 1 to 5, characterized in that the at least one plant, non-mammalian animal and/or microbial protease is administered to an individual in an amount of 1 to 100 mg/kg, preferably 2 to 50 mg/kg, more preferably 5 to 20 mg/kg body weight.

7. Use set forth in any one of items 1 to 6, characterized in that the medicament further includes at least one pharmaceutical acceptable carrier, diluent and/or excipient, preferably a binder, a filler, a disintegrant, a lubricant, a preservative and/or a coating.

8. Use set forth in any one of items 1 to 7, characterized in that the medicament is adapted for intraocular, oral, topical, enteral or parenteral administration.

9. Use set forth in any one of items 1 to 8, characterized in that the medicament is provided in a pharmaceutical form selected from the group consisting of eye drops, ear drops, nasal drops, nasal spray, tablets, preferably soluble tablets, effervescent tablets, gastro-resistant tablets and sublingual tablets, capsules, preferably gastro-resistant capsules, powders, granules, oral liquids, oral drops, ointments, lotions, emulsions, hydrogels, suppositories, pessaries, infusions and injections.

10. Use set forth in any one of items 1 to 9, characterized in that the medicament further includes at least one further active ingredient.

11. Use set forth in item 10, characterized in that the at least one further active ingredient is a flavonoid and/or an antioxidant.

12. Use set forth in item 11, characterized in that the flavonoid is rutin.

13. Use set forth in any one of items 10 to 12, characterized in that the further active ingredient is included in the medicament in an amount from 5 to 35% w/w, preferably from 10 to 30% w/w, more preferably from 15 to 25% w/w.

14. Use set forth in any one of items 1 to 13, characterized in that the medicament includes at least one protease selected from the group consisting of bromelain, papain, ficin, nattokinase, brinase, pronase, serrapeptase, reptilase, krill enzyme, batroxobin, lumbrokinase, cucumisin, subtilisin, seaprose and optionally a further active ingredient, wherein said further active ingredient is preferably a flavonoid, in particular rutin.

BRIEF DESCRIPTION OF THE DRAWINGS

The present invention is further illustrated by the following figures and examples.

FIG. 7 (right) shows the inhibition of VEGF induced tube formation in HUVEC. Bromelain, ficin, nattokinase, papain and serrapeptase, but not chymotrypsin or trypsin inhibited formation of tubes almost to the same extend as in untreated HUVEC.

DETAILED DESCRIPTION OF THE INVENTION

Figure 1:
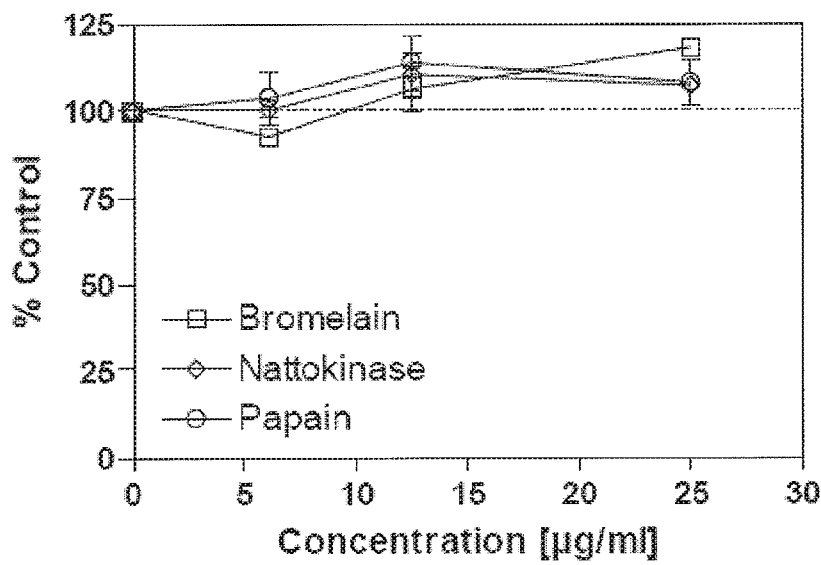
FIG. 1 shows the LDH release into the supernatant of enzyme treated HUVEC (toxicity testing).

It is an object of the present invention to provide medicaments for treating or preventing eye diseases related to neoangiogenesis.

Therefore, the present invention relates to the use of at least one protease for the manufacture of a medicament for the treatment and/or prevention of ocular diseases related to neoangiogenesis selected from the group consisting of age related macular degeneration (AMD), choroidal neovascularisation, Hippel-Lindau Disease, iris neovascularisation, ischemic proliferative retinopathy, neovascularisation of the Cornea and proliferative sickle cell retinopathy, wherein the at least one protease is selected from the group consisting of plant, non-mammalian animal and microbial proteases.

It was surprisingly found that in particular a medicament comprising a combination of at least one protease, which is preferably selected from the group consisting of plant, non-mammalian animal and microbial proteases, allows—when administered to an individual—to reduce significantly (at least 40%, preferably at least 50%, more preferably at least 60%, even more preferably at least 70%, most preferably at least 80%, in particular at least 90%, compared to the VEGF level of said individual prior the administration of the medicament according to the present invention) the level of VEGF and, thus, reducing angiogenesis. Therefore, at least one, preferably a combination of at least two (at least three, at least four, at least five, at least six), proteases can be used to prevent and/or to treat eye diseases related to neoangiogenesis in an individual. The administration of microbial, non-mammalian animal and plant proteases is especially suited because said proteases do not show significant toxicity when contacted with human or animal cells, in particular with endothelial cells. Even a combination of proteases as disclosed herein is not toxic to an animal or human, but acts on angiogenesis.

Interestingly, it could be shown that proteases of mammalian (i.e. human and animal) origin like trypsin or chymotrypsin are not able to inhibit or prevent angiogenesis. Therefore the sole administration of such proteases to an individual may not be used for preventing or treating diseases related to neoangiogenesis.

The term "medicament" as defined herein includes not only pharmaceutical products but also dietary supplements.

As used herein, "plant proteases" and "animal proteases" and "non-mammalian animal protease" are intended to be proteases naturally occurring in plants or non-mammalian animals and being extracted or obtained therefrom. "Plant proteases" and "animal proteases" and "non-mammalian animal protease" are also recombinant proteases whose encoding DNA (e.g. as cDNA) is derived or obtained from a plant and animal (comprising said DNA naturally in its genome), respectively, and cloned into appropriate vectors and expressed in a prokaryotic (e.g. bacterial) or an eukaryotic (e.g. insect cell, mammalian cell) cell culture.

"Microbial proteases", as used herein, are proteases naturally occurring in microorganisms, such as bacteria and fungi (e.g. yeast, moulds). Said proteases may, however, be isolated also from other cells or organisms, provided that said cells and organisms harbor the DNA of the microbial protease and are able to produce recombinantly said protease.

The use of the medicament according to the present invention is particularly suited if the eye disease related to angiogenesis to be treated and/or prevented is selected from the group listed above. All these diseases show increased angiogenesis mostly due to an increased level of vascular endoithelial growth factor (VEGF) in the body. However, it is in particular preferred to use the medicament of the present invention to treat age related macular degeneration.

Several diseases are related to neoangiogenesis for which the medicament of the present invention may also be used.

Neovascularisation of the eye, for instance, is the most frequent cause of blindness (Age related Macular Degeneration; Hippel-Lindau Disease; Behcet's syndrome; idiopathic ocular neovascularisation).

It is especially preferred to use the medicament of the present invention to prevent and/or treat individuals suffering from diseases caused by high VEGF levels and associated to angiogenesis, whereby these diseases are not mainly or completely associated with increased proliferative activity.

The at least one plant protease is preferably selected from the group consisting of bromelain, papain, ficin and cucumisin.

The plant proteases preferably to be used according to the present invention are listed above.

These proteases may be obtained by recombinant expression in a host or by extraction from a plant naturally producing said proteases, whereby the extract itself may directly be used to manufacture the medicament according to the present invention. Extraction methods of the proteases are well known in the art.

For instance, Bromelain is prepared from the stump or root portion of the pineapple plant after harvest of the fruit. This stump or root portion is collected from the fields, peeled and crushed to extract the juice containing the soluble Bromelain enzyme. Further processing includes precipitation of the enzyme to further purify it.

Papain may be produced as a crude, dried material by collecting the latex from the fruit of the *papaya* tree. The latex is collected after scoring the neck of the fruit whereupon it may either dry on the fruit or drip into a container. This latex is then further dried. It is now classified as a dried, crude material. A purification step is necessary to remove contaminating substances. This purification consists of the solubilization and extraction of the active papain enzyme.

According to a preferred embodiment of the present invention the microbial protease is selected from the group consisting of nattokinase, brinase, pronase, seaprose, serrapeptase and subtilisin.

Microbial proteases may also be obtained by recombinant techniques or may be isolated directly from microbial cultures comprising the microorganisms which produce said proteases.

Nattokinase, for instance, is obtained from natto, a traditional Japanese food product made from fermented soybeans, or by cultures comprising organisms of a specific *Bacillus subtilis* subspecies (*Bacillus subtilis* var. natto) which are able to produce said protease. *Bacillus subtilis* var. natto may be isolated from natural soil and Japanese commercial natto. The strain has ability to produce a high activity of nattokinase products which degrade fibrin. Carbon sources, organic nitrogen sources or inorganic nitrogen sources, mineral salts, initial pH and temperatures have to be optimized for nattokiase production from *B. subtilis* var. natto. It was found, for instance, that the optimal inoculum size of *B. subtilis* var. natto is around 5% (v/v). The optimal medium may contain 2.8% soybean protein, 1% yeast extract, and 0.8% maltose. Furthermore, the optimal pH and temperature may be around 6.5±0.5 and around 30° C. to 40° C., respectively. The optimal incubation period is 18 to 48 hours. Nattokinase activity in the fermentation medium may increase to over 40 FU/ml.

Serrapeptase, for instance, is a proteolytic enzyme isolated from *Serratia* E15 bacteria, located in the gut of silkworms. This enzyme can be used as a supplement to treat pain and inflammation naturally, and is in clinical use in parts of Asia and Europe. Serrapeptase is used as an alternative to Non Steroidal Anti-Inflammatory Drugs (NSAIDS) which are commonly used to treat arthritis and inflammation.

The non-mammalian animal protease is preferably selected from the group consisting of reptilase, krill enzyme, batroxobin and lumbrokinase.

These proteases may be produced recombinantly by methods known in the art or obtained directly from the respective animals.

Particularly preferred medicaments comprise bromelain and/or papain as plant proteases and optionally nattokinase as microbial protease. The preferred ratios between these proteases in a medicament according to the present invention can be found in the following table, whereby the amount of papain, nattokinase and/or bromelain may vary-independently from each other-between 0 and 80%, preferably 10 to 75%, more preferably 15 (or 16,67) to 75% of the total amount of protease present in the medicament.

| Bromelain | Nattokinase | Papain |
|---|---|---|
| 75.00% | 25.00% | 0.00% |
| 16.67% | 16.67% | 66.67% |
| 25.00% | 25.00% | 50.00% |
| 0.00% | 75.00% | 25.00% |
| 75.00% | 0.00% | 25.00% |
| 25.00% | 0.00% | 75.00% |
| 16.67% | 66.67% | 16.67% |
| 50.00% | 0.00% | 50.00% |
| 0.00% | 50.00% | 50.00% |
| 0.00% | 25.00% | 75.00% |
| 33.33% | 33.33% | 33.33% |
| 25.00% | 75.00% | 0.00% |
| 50.00% | 25.00% | 25.00% |

According to another preferred embodiment of the present invention the at least one plant, non-mammalian animal and/or microbial protease is comprised in the medicament in an amount from 10 to 90% w/w, preferably from 20 to 80% w/w, more preferably from 30 to 70% w/w.

The at least one plant, non-mammalian animal and/or microbial protease is preferably administered to an individual in an amount of 1 to 100 mg/kg, preferably 2 to 50 mg/kg, more preferably 5 to 20 mg/kg body weight.

The medicament may preferably further comprise at least one pharmaceutical acceptable carrier, diluent and/or excipient, preferably a binder, a filler, a disintegrant, a lubricant, a preservative and/or a coating.

Depending on the pharmaceutical formulation of the medicament according to the present invention various other substances like excipients, coatings etc. may be used.

Furthermore, the medicament of the present invention may preferably be adapted for oral, topical, enteral or parenteral administration.

According to a preferred embodiment of the present invention the medicament is provided in a pharmaceutical form selected from the group consisting of eye drops, ear drops, nasal drops, nasal spray, tablets, preferably soluble tablets, effervescent tablets, gastro-resistant tablets and sublingual tablets, capsules, preferably gastro-resistant capsules, powders, granules, oral liquids, oral drops, ointments, lotions, emulsions, hydrogels, suppositories, pessaries, infusions and injections.

In a particular preferred embodiment of the present invention, the medicament is adapted for oral administration. This mode of administration is non-invasive and therefore allows a repeated administration (without harming the patient) of the medicament.

The medicament of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

Examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as colouring agents, release agents, coating agents, sweetening, flavouring and perfuming agents, preservatives and antioxidants can also be present in the medicament according to the present invention. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alphatocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient which can be combined with a carrier material to produce a single dosage form will generally be that amount of the compound which produces a therapeutic effect.

Methods of preparing the medicaments and formulations according to the present invention include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product. Formulations of the invention suitable for oral administration may be in the form of capsules, cachets, pills, tablets, lozenges (using a flavoured basis, usually sucrose and acacia or tragacanth), powders, granules, or as a solution or a suspension in an aqueous or non-aqueous liquid, or as an oil-in-water or water-in-oil liquid emulsion, or as a syrup, or as pastilles (using an inert base, such as gelatin and glycerin, or sucrose and acacia), each containing a predetermined amount of a protease combination of the present invention as active ingredients.

The proteases of the present invention may also be administered as a bolus, electuary or paste. In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agaragar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) colouring agents.

In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract or, optionally, in a delayed manner. Examples of embedding compositions which can be used include polymeric substances and waxes. The proteases can also be in microencapsulated form, if appropriate, with one or more of the above-described excipients. Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, polyethylene glycols and fatty acid esters of sorbitan, and mixtures thereof. Besides inert diluents, the oral compositions can also include adjuvants such as wetting agents, emulsifying and suspending agents, sweetening, flavouring, colouring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the proteases of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate. Dosage forms for the topical or transdermal administration of a compound of this invention include powders, sprays, ointments, pastes, creams, lotions, gels, solutions, patches and inhalants. The proteases may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the proteases of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the proteases of the present invention to the body. Such dosage forms can be made by dissolving or dispersing the proteases in the proper medium. Absorption enhancers can also be used to increase the flux of the proteases across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise the proteases of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms upon the subject compositions may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. In some cases, in order to prolong the effect of a drug, it is desirable to slow the absorption of the drug from subcutaneous or intramuscular injection. This may be accomplished by the use of a liquid suspension of crystalline or amorphous material having poor water solubility. Alternatively, delayed absorption of a parenterally-administered drug form is accomplished by dissolving or suspending the drug in an oil vehicle. Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides).

Depot injectable formulations are also prepared by entrapping the drug in liposomes or microemulsions which are compatible with body tissue. When the proteases of the present invention are administered as pharmaceuticals, to humans and animals, they can be given per se or as a pharmaceutical composition containing, for example, 0.1 to 99.5% (more preferably, 0.5 to 90%) of the proteases in combination with a pharmaceutically acceptable carrier. The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral and topical administrations are preferred.

The phrases "parenteral administration" and "administered parenterally" as used herein mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The medicament of the present invention may be administered to humans and other animals for therapy by any suitable route of administration, including orally, nasally, as by, for example, a spray, rectally, intravaginally, parenterally, intracisternally and topically, as by powders, ointments or drops, including buccally and sublingually. Regardless of the route of administration selected, the proteases of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular protease of the present invention employed, the route of administration, the time of administration, the rate of excretion of the particular compound being employed, the duration of the treatment, other drugs, compounds and/or materials used in combination with the proteases employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the proteases of the invention employed in the pharmaceutical composition at levels lower than that required in order to achieve the desired therapeutic effect and gradually increase the dosage until the desired effect is achieved.

While it is possible for the proteases of the present invention to be administered alone, it is preferable to administer the proteases as a pharmaceutical formulation (composition).

According to another preferred embodiment of the present invention the medicament further comprises at least one further active ingredient.

Said active ingredient may be any one which may support the prevention and the treatment of angiogenic diseases with the proteases according to the present invention. However, it is of course also possible to add active ingredients exhibiting other effects than said proteases.

The at least one further active ingredient is preferably selected from the group consisting of flavonoids, in particular bioflavonoids, antioxidants or other substances like white willow bark extract.

According to another preferred embodiment of the present invention the medicament comprises at least one (two, three or even four) proteases selected from the group consisting of bromelain, papain, ficin, nattokinase, brinase, pronase, serrapeptase, reptilase, krill enzyme, batroxobin, lumbrokinase, cucumisin, subtilisin, seaprose and optionally a further active ingredient, wherein said further active ingredient is preferably a flavonoid, in particular rutin.

According to a preferred embodiment of the present invention the flavonoid is selected from the group consisting of rutin or derivatives thereof.

Bromelain and papain, for instance, are referred to as thiol proteases and contain a cysteine residue at the active site. Under oxidizing conditions the thiol group of this cysteine loses a hydrogen atom and may crosslink with another thiol group, forming a disulfide bridge or, alternatively, crosslinking with another residue through the same oxidative process. In this oxidized state, the bromelain and papain lose activity. Through the inclusion of antioxidant vitamin C, bioflavonoids like rutin and proanthocyanidins the oxidation of the active sulfhydryl group of the thiol proteases can be prevented.

Said further active ingredient is preferably comprised in the medicament of the present invention in an amount from 5 to 35% w/w, preferably from 10 to 30% w/w, more preferably from 15 to 25% w/w.

EXAMPLES

Materials:
Bromelain from Pineapple stem with an activity of 3.51 U/mg was obtained from Sigma Aldrich, Austria
Nattokinase with an activity of 10.000 U/ml was purchased from Japan Bio Science Laboratory Co, Ltd.
Papain from *Carica Papaya* with an activity of >3 U/mg was obtained from Sigma Aldrich, Austria Example 1: Toxicity-Test The antiproliferative activity of bromelain, nattokinase and papain was assessed using a Lactate Dehydrogenase (LDH) Assay. Human Umbilical Vein Endothelial Cells (HUVEC) from semi-confluent cultures were harvested by treatment with trypsin, seeded at a density of 2500 cells/well into 96-well microplates, previously coated with human fibronectin. In oder to allow proper attachment, cells were incubated for 24 hours in Endothelial Basal medium 2MV (Cambrex Biochemicals) containing 10% Fetal Calf Serum, 60 µg/ml Endothelial cell Growth Supplement, hrEGF, hrFGF2, hrIGF, hrVEGF, Ascorbic Acid and Heparin. After attachment, cells were starved by incubation at 37° C./95% humidity in Medium 199+10% Fetal Calf Serum (FCS) without growth factors. After 24 hours, the supernatant was replaced by Medium 199 containing 10% FCS, VEGF and varying concentrations of the enzymes. After an incubation period of 48 hours, supernatant was harvested and an LDH assay was performed according to the instructions of the manufacturer (Promega, Germany): 50 µl aliquots from all wells were transferred to a fresh 96-well flat-bottom (enzymatic assay) plate. The Assay Buffer was added to the Substrate Mix and mixed gently. 50 µl of reconstituted Substrate Mix was added to each well. The plate was incubated for 30 minutes at room temperature. 50 µl of Stop Solution was added to each well. Within one hour, optical density was measured at 490 nm with a reference wavelength of 620 nm. Results are expressed as % untreated control.

The results are shown in FIG. 1. They clearly demonstrate that bromelain, nattokinase and papain up to a level of including 25 µg/ml did not show toxic effects on HUVEC after 2 days of incubation.

Example 2: Antiproliferative Activity

The antiproliferative activity of bromelain, nattokinase and papain and their mixtures was assessed using an 3-(4, 5-dimethylthiazol-2-yl)-2,5-diphenyltetrazoliumbromide (MTT) assay. Human Umbilical Vein Endothelial Cells (HUVEC) from semi-confluent cultures were harvested by treatment with trypsin seeded at a density of 1000 cells/well into 96-well microplates, previously coated with human fibronectin. In order to allow proper attachment, cells where incubated for 24 hours in Endothelial Basal medium 2MV (Cambrex Biochemicals) containing 10% Fetal Calf Serum, 60 µg/ml Endothelial cell Growth Supplement, hrEGF, hrFGF2, hrIGF, hrVEGF, ascorbic acid and heparin. After attachment, cells were starved by incubation at 37° C./95% humidity in Medium 199+10% Fetal Calf Serum (FCS) without growth factors. After 24 hours, the supernatant was replaced by Medium 199 containing 10% FCS and varying concentrations of bromelain, nattokinase and papain. Cells were incubated further 48 hours at 37° C./95% humidity. The MTT Assay was carried out using an EZ4U MTT Kit (Biomedica, Austria; according to the instructions of the manufacturer). Optical density was measured at 450 nm with a reference wavelength of 620 nm. Results are expressed as % proliferation with 100% being the proliferation of the VEGF treated control.

Figure 2:
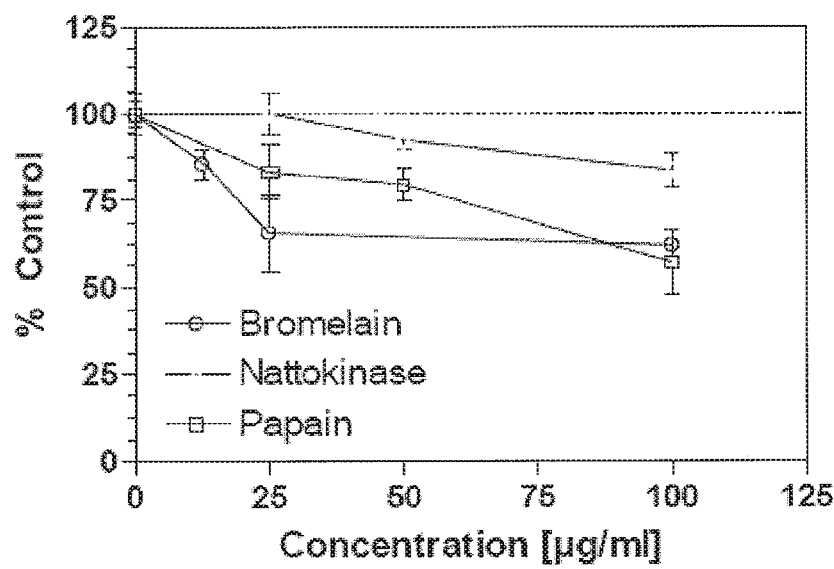
FIG. 2 shows a MTT assay with enzyme treated HUVEC (antiproliferative activity).

The results of the concentration-response experiments are shown in FIG. 2. They demonstrate a clear antiproliferative effect of bromelain, nattokinase and papain with bromelain and papain reaching 75% growth at concentrations as low as 25 µg/ml. Taken together with the results from the LDH release test, these data point towards a clear antiproliferative, but not cytotoxic activity.

The results of the mixtures are shown in table 1. A clear antiproliferative effect can be seen.

TABLE 1

Growth inhibition of HUVEC of combinations of bromelain, nattokinase and papain in presence of VEGF.

| Bromelain | Nattokinase | Papain | % Proliferation |
|---|---|---|---|
| 0.00% | 0.00% | 100.00% | 75.45% |
| 75.00% | 0.00% | 25.00% | 89.09% |
| 16.67% | 16.67% | 66.67% | 91.82% |
| 25.00% | 75.00% | 0.00% | 94.55% |
| 66.67% | 16.67% | 16.67% | 96.82% |

Example 3: Antiangiogenic Activity

Methods: Antiangiogenic activity was assessed using a tube formation assay. Growth factor reduced Matrigel (Becton Dickinson, Vienna) was thawed at a temperature of 4° C. 50 µl per well were pipetted into the wells of a 96 well microtiter plate. The plate was left at 4° C. for 24 hours. Prior to the experiment, the plate was incubated for 30-60 minutes at 37° C. to solidify the gel. HUVEC were harvested by treatment with trypsin and seeded into Matrigel coated 96 well microplates at a density of 20.000 cells per well in Endothelial Growth Medium 2(MV) (Lonza, Brussels) supplemented with ascorbic acid and hydrocortisone according to the instructions of the manufacturer as well as 5000 U/ml heparin and 1% Fetal Bovine Serum. Drugs and VEGF were added to the desired concentrations. After further 16 hrs to 18, wells were photographed. The total length of tubes was determined using the ImageJ Software, measured by the Neuron Length Determination Plugin.

Results

Figure 3:
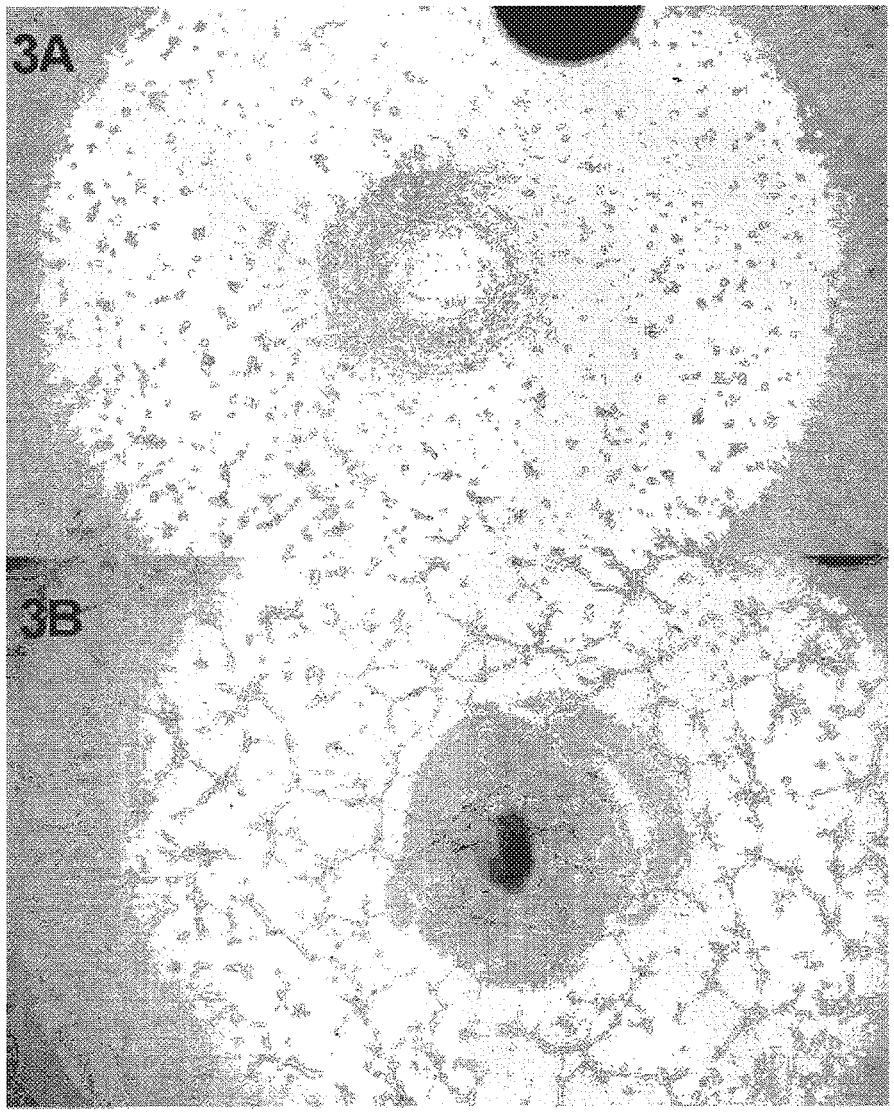
FIG. 3A shows the inhibition of VEGF induced tube formation by combination of 25% Bromelain, 50% nattokinase and 25% papain.
FIG. 3B shows the control treated with VEGF only. Whereas in the VEGF control a narrow pattern of formed tubes is visible, the enzyme treated sample shows wide areas of non-tube formation indicating antiangiogenic activity of the enzyme cocktail.
Figure 7:
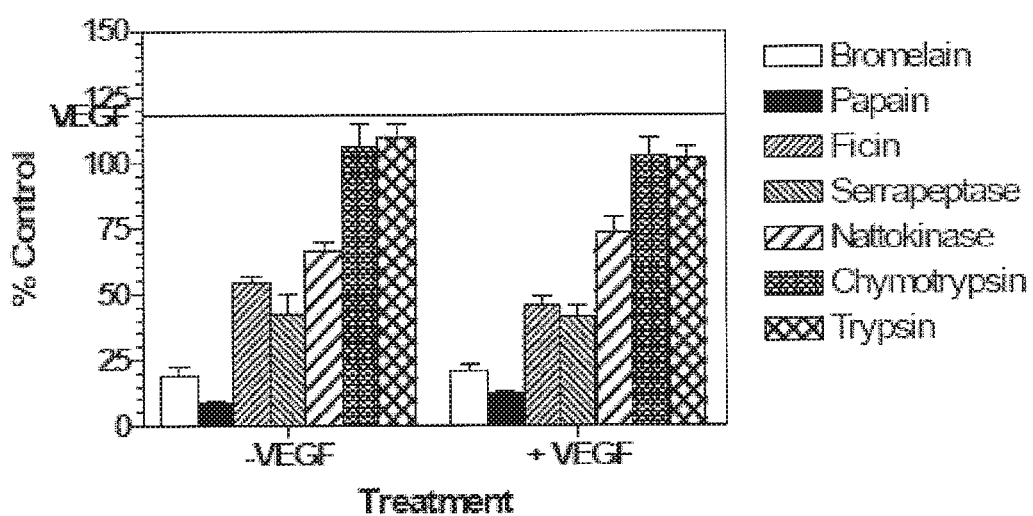
FIG. 7 (left) shows the inhibition of spontaneous tube formation in HUVEC. Bromelain, ficin, nattokinase, papain and serrapeptase, but not chymotrypsin or trypsin inhibited formation of tubes.

The results of the tube formation assays of enzymes and enzyme mixtures are shown in FIG. 3, FIG. 7 and table 1.

Table 1 shows the inhibition of tube formation by various mixtures of bromelain, nattokinase and papain. Results clearly indicate
1. Tube formation is inhibited by the enzymes bromelain, ficin, nattokinase, papain and serrapeptase.
2. The combination of bromelain, nattokinase and papain has a greater effect than these drugs alone.

TABLE 1

Tube formation (% controls) in HUVEC in presence of VEGF.

| Bromelain | Nattokinase | Papain | % tube formation |
|---|---|---|---|
| 75.00% | 25.00% | 0.00% | 1.89% |
| 16.67% | 16.67% | 66.67% | 6.48% |
| 25.00% | 25.00% | 50.00% | 12.25% |
| 0.00% | 75.00% | 25.00% | 12.58% |
| 75.00% | 0.00% | 25.00% | 13.66% |
| 25.00% | 0.00% | 75.00% | 16.23% |
| 16.67% | 66.67% | 16.67% | 16.35% |
| 0.00% | 0.00% | 0.00% | 16.60% |
| 50.00% | 0.00% | 50.00% | 17.27% |
| 0.00% | 50.00% | 50.00% | 19.99% |
| 0.00% | 25.00% | 75.00% | 21.74% |
| 33.33% | 33.33% | 33.33% | 25.86% |
| 25.00% | 75.00% | 0.00% | 38.43% |
| 0.00% | 0.00% | 0.00% | 40.64% |
| 50.00% | 25.00% | 25.00% | 52.22% |
| 0.00% | 0.00% | 100.00% | 60.14% |
| 0.00% | 0.00% | 0.00% | 100% |

Results are shown as % tube formation with 100% equaling tube formation in samples treated with VEGF only.
Combinations not shown did not inhibit tube formation.

Conclusions

A significant decrease in the VEGF mediated formation of microvessel like tubes was detected after treatment with bromelain, ficin, nattokinase, papain or serrapeptase alone, and after treatment with a mixture of the enzymes bromelain, nattokinase and papain.

Example 4

In this example the effect of an enzyme therapy (enzyme mixture: nattokinase, bromelain, papain+rutin bioflavonoid, white willow bark extract) on the amount of VEGF concentration in blood was studied. It could be shown (see results below), that the enzyme therapy significantly reduces elevated VEGF concentration in human blood.

Trial was performed as randomized, open label, multi-centre pilot study on 111 diabetic typ 2 patients of both genders in two parallel, comparable groups. 54 patients got an enzyme mixture (nattokinase (20 000 FU/gm) 25 mg bromelain (2450 GDU/gm) 90 mg papain N.F. (2.400 USP Units/mg). 100 mg rutin bioflavonoid complex (rutosides & rutinosides) 120 mg White willow bark extract (15% salicin/7% polyphenols) 100 mg, Marlyn Nutraceuticals, USA) for 4 weeks. VEGF concentrations in patients' plasma were tested before supplementation and right after 4 weeks of supplementation. Patients served themselves as self-control with their initial values.

Figure 4:
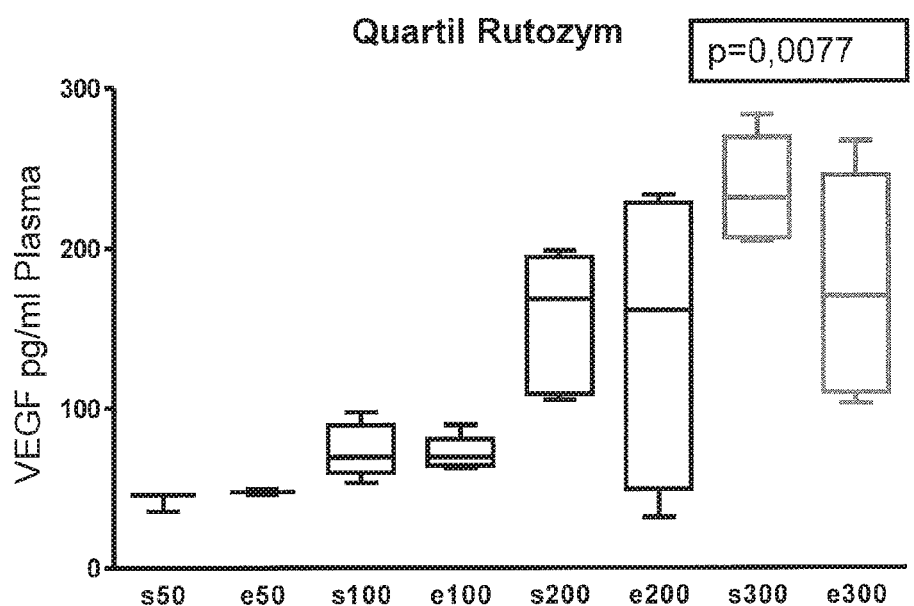
FIG. 4 shows the VEGF concentrations in blood of patients treated with Rutozym.

VEGF concentrations in blood were separated in 4 different groups (quartiles; see FIG. 4): VEGF concentration in patients blood before therapy <50 ng/ml; (s50=start<50 ng/ml; e50=end) s100: VEGF concentration<100 ng/ml before therapy; s200: <200 ng/ml before therapy and s300: >200 ng VEGF before therapy. It could be shown that the use of a medicament according to the present invention comprising proteases of plant and/or microbial sources can be used to reduce the VEGF level in blood and, thus, be used for the treatment of diseases related to neoangiogenesis.

Example 5: Antiproliferative Effects of Rutosid on HUVEC

To assess a possible antiproliferative activity of Rutosid an 3-(4,5-dimethylthiazol-2-yl)-2,5-diphenyltetrazolium-bromide (MTT) Assay was used. Human Umbilical Vein Endothelial Cells (HUVEC) from semi-confluent cultures were harvested by treatment with trypsin seeded at a density of 1000 cells/well into 96-well microplates, previously coated with human fibronectin. In order to allow proper attachment, cells were incubated for 24 hours in Endothelial Basal medium 2MV (Cambrex Biochemicals) containing 10% Fetal Calf Serum, 60 µg/ml Endothelial cell Growth Supplement, hrEGF, hrFGF-2, hrIGF, hrVEGF, ascorbic acid and heparin. After attachment, cells were starved by incubation at 37° C./95% humidity in Medium 199+10% Fetal Calf Serum (FCS) without growth factors. After 24 hours, the supernatant was replaced by Medium 199 containing 10% FCS and varying concentrations of Rutosid and VEGF. Cells were incubated further 48 hours at 37° C./95% humidity. The MTT-Assay was carried out using a EZ4U MTT Kit (Biomedica, Austria) according to the instructions of the manufacturer) Optical density was measured at 450 nm with a reference wavelength of 620 nm. Results are expressed as % proliferation with 100% being the proliferation of the VEGF treated control.

Figure 5:
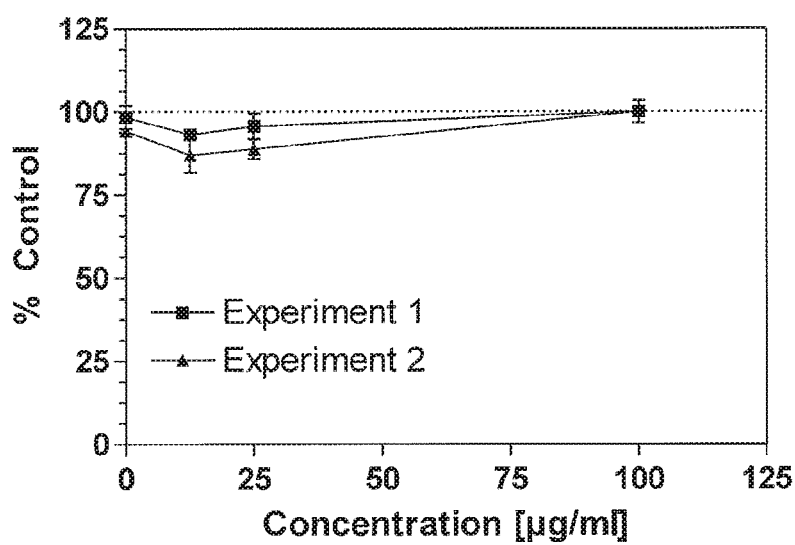
FIG. 5 shows an MTT-Assay with VEGF stimulated HUVEC and Rutosid. No inhibition of proliferation can be seen.

The results clearly indicate that rutosid does not inhibit VEGF stimulated proliferation of HUVEC (see FIG. 5).

Example 6: Toxic Effects of Rutosid on HUVEC

To test a possible cytotoxic activity of rutosid an Lactate Dehydrogenase (LDH) Assay was used. Human Umbilical Vein Endothelial Cells (HUVEC) from semi-confluent cultures were harvested by treatment with trypsin, seeded at a density of 2500 cells/well into 96-well microplates, previously coated with human fibronectin. In oder to allow proper attachment, cells were incubated for 24 hours in Endothelial Basal medium 2MV (Cambrex Biochemicals) containing 10% Fetal Calf Serum, 60 µg/ml Endothelial cell Growth Supplement, hrEGF, hrFGF-2, hrIGF, hrVEGF, ascorbic acid and heparin. After attachment, cells were starved by incubation at 37° C./95% humidity in Medium 199+10% Fetal Calf Serum (FCS) without growth factors. After 24 hours, the supernatant was replaced by Medium 199 containing 10% FCS, VEGF and varying concentrations of the enzymes. After an incubation period of 48 hours, supernatant was harvested and an LDH assay was performed according to the instructions of the manufacturer (Promega, Germany): 50 µl aliquots from all wells where transferred to a fresh 96-well flat-bottom (enzymatic assay) plate. The Assay Buffer was added to the Substrate Mix and mixed gently. 50 µl of reconstituted Substrate Mix was added to each well. The plate was incubated for 30 minutes at room temperature. 50 µl of Stop Solution were added to each well. Within one hour, optical density was measured at 490 nm with a reference wavelength of 620 nm. Results are expressed as % untreated control.

Figure 6:
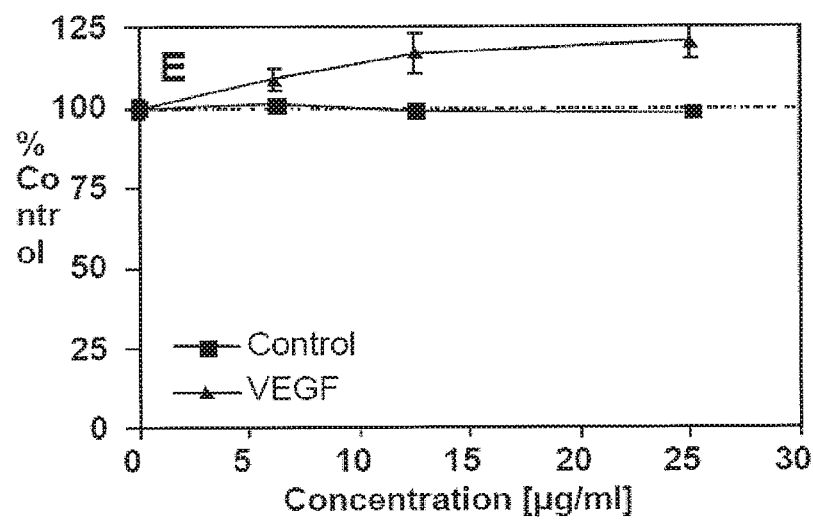
FIG. 6 shows the toxic effects of Rutosid on HUVEC. No toxic effects could be seen in quiescent HUVEC, whereas VEGF activated HUVEC show a slight effect.

The results clearly indicate, that the toxicity of rutosid is negligible in HUVEC (see FIG. 6).

Example 7: Inhibition of VEGF in the Mouse Models of Oxygen-Induced Retinopathy and Laser-Induced Choroidal Neovascularisation by Proteases from Plants Angioproliferative retinopathy is a major cause for severe loss of vision in industrialized countries. Underlying diseases are diabetes, retinal vein occlusion, retinopathy of prematurity or late stages of age-related macular degeneration (AMD). The standard therapy for ischemic retinal disease is based on the destruction of peripheral retinal tissue to minimize the production of angiogenic factors like VEGF. Since the destruction of neuronal tissue is irreversible, a local treatment with inhibitors of angiogenic factors would be desirable to protect patients who have an increased risk of developing retinal or choroidal neovascularisation. In AMD, the local treatment with angioinhibitory drugs became standard of care in the meantime.

Methods

A. Oxygen-induced Retinopathy (OIR)

A mouse model of oxygen-induced retinopathy (OIR) was established as described by Smith and colleagues (Invest. Ophthalmol. Vis. Sci. (1994) 35: 101-111) 7 days (P7) old C57/B16J mice were placed in 75% oxygen until P12. After return to normal oxygen, the animals developed retinal neovascularisation due to relative hypoxia. This effect was influenced by a test substance injected intravitreally in one eye while a control solution was injected in the other eye. Retinal proliferation was evaluated at P17 by flatmounts after perfusion with fluorescein dextran. These wholemounts allow to evaluate the vascular changes of the retinal vasculature in a coded fashion. Scores according to a scoring system were determined for each flatmount and compared by the Wilcoxon matched-pairs signed-ranks test resulting in a significant difference between treatment and control. A total of 30 mice per group was used.

In a second test the test substance was injected IP at P12. In this case, an intra-individual comparison between the two eyes was not possible and therefore, an extra control group was necessary. A total of 25 mice per group was used.

B. Laser-Induced Choroidal Neovascularisation (Laser-CNV)

A mouse model for laser-induced choroidal neovascularisation was established as described by Campochiaro and colleagues (Tobe et al., Am. J. Pathol. (1998) 153: 1641-1646. C57/B16J mice not younger than 12 weeks were anesthetized, and neovascularisation was induced with 3 visually controlled laser burns to the retina at day 0 (d0). The animals developed choroidal neovascularisation at the laser sites within two weeks after wounding. At d7 or at several days, a test substance was injected intravitreally into one eye and a control solution into the other eye to see if there was an influence on retinal or choroidal angiogenesis. 13 days later, at d14, the animals were perfused with dextranfluorescein, and choroidal whole-mounts were prepared. The whole-mounts allow evaluating the vascular changes of the chlorid and the size of the CNV-membrane. The values for each laser spot were compared by the Wilcoxon matced-pairs signed-ranks test resulting in a significant difference between treatment and control. A total of 30 mice per group was used.

In a further experiment the test substance was injected IP at P7 or at several days. In this case, an intraindividual comparison between the two eyes was not possible and therefore, and extra control group was necessary. A total of 25 mice per group was used.

The invention claimed is:

1. A method of treating ocular diseases related to neoangiogenesis comprising administering orally to an individual in need thereof, a therapeutically effective amount of at least bromelain and papain to reduce vascular endothelial growth factor (VEGF) induced tube formation related to ocular neoangiogenesis; wherein the ocular disease related to neoangiogenesis is selected from the group consisting of age related macular degeneration (AMD), choroidal neovascularisation, Hippel-Lindau Disease, iris neovascularisation, ischemic proliferative retinopathy, neovascularisation of the Cornea, and proliferative sickle cell retinopathy.

2. The method according to claim 1, wherein the bromelain and papain are administered in a medicament in an amount from 10 to 90% w/w.

3. The method according to claim 1, wherein the bromelain and papain are administered to an individual in an amount of 1 to 100 mg/kg body weight.

4. The method according to claim 1, wherein the bromelain and papain are administered in a medicament comprising at least one pharmaceutical acceptable carrier, diluent and/or excipient.

5. The method according to claim 1, wherein the bromelain and papain are administered in a tablet.

6. The method according to claim 1, wherein the bromelain and papain are administered in a medicament comprising at least one further active ingredient.

7. The method according to claim 6, wherein the at least one further active ingredient is a flavonoid and/or an antioxidant.

8. The method according to claim 7, wherein the flavonoid is rutin.

9. The method according to claim 6, wherein the further active ingredient is present in the medicament in an amount from 5 to 35% w/w.

10. The method according to claim 1, wherein the bromelain and papain are administered in a medicament comprising optionally a further active ingredient.

11. The method according to claim 1, wherein the bromelain and papain are administered in a medicament in an amount from 20 to 80% w/w.

12. The method according to claim 1, wherein the bromelain and papain are administered in a medicament in an amount from 30 to 70% w/w.

13. The method according to claim 1, wherein the bromelain and papain are administered to an individual in an amount of 2 to 50 mg/kg body weight.

14. The method according to claim 1, wherein the bromelain and papain are administered to an individual in an amount of 5 to 20 mg/kg body weight.

15. The method according to claim 6, wherein the further active ingredient is present in the medicament in an amount 10 to 30% w/w.

16. The method according to claim 6, wherein the further active ingredient is present in the medicament in an amount from 15 to 25% w/w.

17. The method according to claim 1, wherein the bromelain and papain are administered in a medicament comprising a binder, a filler, a disintegrant, a lubricant, a preservative and/or a coating.

18. The method according to claim 1, wherein the bromelain and papain are administered in a medicament provided in a pharmaceutical form selected from the group consisting of soluble tablets, effervescent tablets, gastro-resistant tablets, sublingual tablets, and capsules.

19. The method according to claim 1, wherein the bromelain and papain are administered in a medicament provided in a pharmaceutical form selected from the group consisting of gastro-resistant capsules, powders, granules, oral liquids, and oral drops.

20. The method according to claim 10, wherein the further active ingredient is a flavonoid.

21. The method according to claim 20, wherein the flavonoid is rutin.

22. A method of reducing vascular endothelial growth factor (VEGF) level in an individual with an increased risk of developing ocular disease related to neoangiogenesis comprising orally administering to the individual in need thereof, a composition comprising bromelain and papain in an effective amount to reduce VEGF level related to ocular neoangiogenesis; wherein the ocular disease related to neoangiogenesis is selected from the group consisting of age related macular degeneration (AMD), choroidal neovascularisation, Hippel-Lindau Disease, iris neovascularisation, ischemic proliferative retinopathy, neovascularisation of the Cornea, and proliferative sickle cell retinopathy.

* * * * *